(12) United States Patent
Naganawa et al.

(10) Patent No.: US 11,224,404 B2
(45) Date of Patent: Jan. 18, 2022

(54) INFORMATION PROCESSING APPARATUS, INFORMATION PROCESSING METHOD, AND NON-TRANSITORY COMPUTER-READABLE STORAGE MEDIUM

(71) Applicant: CANON KABUSHIKI KAISHA, Tokyo (JP)

(72) Inventors: Yoshihiro Naganawa, Yokohama (JP); Hiroyuki Yamamoto, Chigasaki (JP); Takaaki Endo, Urayasu (JP)

(73) Assignee: Canon Kabushiki Kaisha, Tokyo (JP)

( * ) Notice: Subject to any disclaimer, the term of this patent is extended or adjusted under 35 U.S.C. 154(b) by 473 days.

(21) Appl. No.: 15/958,022

(22) Filed: Apr. 20, 2018

(65) Prior Publication Data
US 2018/0310909 A1 Nov. 1, 2018

(30) Foreign Application Priority Data

Apr. 26, 2017 (JP) .............................. JP2017-087593

(51) Int. Cl.
*A61B 8/00* (2006.01)
*G01C 9/06* (2006.01)
*A61B 8/08* (2006.01)

(52) U.S. Cl.
CPC .............. *A61B 8/4245* (2013.01); *A61B 8/40* (2013.01); *A61B 8/5276* (2013.01); *A61B 8/54* (2013.01); *G01C 9/06* (2013.01)

(58) Field of Classification Search
None
See application file for complete search history.

(56) References Cited

U.S. PATENT DOCUMENTS

| 5,969,725 | A | 10/1999 | Fujiki et al. |
| 6,263,100 | B1 | 7/2001 | Oshino et al. |
| 6,628,820 | B2 | 9/2003 | Oshino et al. |
| 8,460,190 | B2 * | 6/2013 | Jackson ................. A61B 8/00 600/437 |

(Continued)

FOREIGN PATENT DOCUMENTS

| JP | 2008-086742 A | 4/2008 |
| JP | 2008-154833 A | 7/2008 |

(Continued)

OTHER PUBLICATIONS

Office Action dated Mar. 12, 2021, in corresponding Japanese Patent Application No. 2017-087593.

*Primary Examiner* — Arleen M Vazquez
*Assistant Examiner* — Terence E Stifter, Jr.
(74) *Attorney, Agent, or Firm* — Venable LLP (57) ABSTRACT

An information processing apparatus includes a memory storing a program, and one or more processors that, by executing the program, function as an obtaining unit configured to obtain information relating to a posture of an imaging device that is imaging a region of a subject, and a determination unit configured to perform a determination, based on the information relating to the posture, regarding which region of the subject corresponds to the region imaged by the imaging device. The determination unit performs the determination based on the information relating to the posture obtained at a timing when a posture of the imaging device satisfies a predetermined condition.

13 Claims, 9 Drawing Sheets

(56) References Cited

U.S. PATENT DOCUMENTS

| | | | |
|---|---|---|---|
| 9,084,556 B2 | 7/2015 | Kakee et al. | |
| 10,417,517 B2 | 9/2019 | Endo et al. | |
| 2004/0109608 A1* | 6/2004 | Love | G06K 9/46 |
| | | | 382/224 |
| 2007/0038152 A1* | 2/2007 | Sarvazyan | A61B 5/681 |
| | | | 600/587 |
| 2007/0064987 A1* | 3/2007 | Esham | A61B 6/504 |
| | | | 382/128 |
| 2007/0239004 A1 | 10/2007 | Kakee et al. | |
| 2008/0154123 A1 | 6/2008 | Jackson et al. | |
| 2009/0076381 A1 | 3/2009 | Motoki et al. | |
| 2012/0044348 A1* | 2/2012 | Pijl | G06T 7/74 |
| | | | 348/135 |
| 2013/0195339 A1* | 8/2013 | Endo | G06K 9/46 |
| | | | 382/131 |
| 2016/0100821 A1* | 4/2016 | Eggers | A61B 8/483 |
| | | | 600/424 |
| 2016/0314587 A1 | 10/2016 | Ishikawa et al. | |
| 2017/0143304 A1* | 5/2017 | Malik | A61B 8/4254 |
| 2018/0271484 A1* | 9/2018 | Whisler | A61B 8/4444 |

FOREIGN PATENT DOCUMENTS

| | | |
|---|---|---|
| JP | 2009-225905 A | 10/2009 |
| JP | 2012-143356 A | 8/2012 |
| JP | 5015580 B2 | 8/2012 |
| JP | 2013-111309 A | 6/2013 |
| JP | 2013-153883 A | 8/2013 |
| JP | 5480472 B2 | 4/2014 |
| JP | 2015-112410 A | 6/2015 |

\* cited by examiner

INFORMATION PROCESSING APPARATUS, INFORMATION PROCESSING METHOD, AND NON-TRANSITORY COMPUTER-READABLE STORAGE MEDIUM

This application claims the benefit of Japanese Patent Application No. 2017-087593, filed Apr. 26, 2017, which is hereby incorporated by reference herein in its entirety.

BACKGROUND OF THE INVENTION

Field of the Invention

The present invention relates to an information processing apparatus, an information processing method, and a non-transitory computer-readable storage medium.

Description of the Related Art

At a medical site, a doctor performs a diagnosis by using medical images imaged by various modalities (imaging apparatuses), such as an ultrasonic diagnosis apparatus, a photoacoustic tomography apparatus (hereafter referred to as a PAT apparatus), a magnetic resonance imaging apparatus (hereafter referred to as an MRI apparatus), a computed tomography apparatus (hereafter referred to as an X-ray CT apparatus), and an optical coherence tomography apparatus (hereafter referred to as an OCT apparatus). In such a case, discriminating, based on information relating to the medical image, what organ (region) of a subject was imaged to produce the medical image, or which one of left and right organs was imaged is useful, and various conventional methods have been proposed.

For example, Japanese Patent No. 5480472 recites a method of, by using characteristics for when imaging the left and right of a subject a plurality of times is performed alternately left and right (left→right→left→right), determining whether an imaged region of a certain time is the left or right of the subject to thereby automatically determine left and right for the remaining times. In addition, Japanese Patent No. 5015580 recites a method of, when registering, by an ultrasonic probe with a position sensor, the position of a papilla of a breast on a side that is imaged, determining based on corresponding position information whether the imaged region is a left breast or a right breast.

However, in the method recited in Japanese Patent No. 5480472, there is a problem in that the initial determination of left or right must be separately performed. In addition, in the method discussed in Japanese Patent No. 5015580, there is a problem in that a means for measuring a position of a base point, such as a papilla, must be prepared, and a problem in that a patient must be present at a predetermined position of a bed.

SUMMARY OF THE INVENTION

The present disclosure provides a mechanism for easily determining an imaged region of a subject in order to solve the problems described above.

According to one aspect, the present invention provides an information processing apparatus that comprises an obtaining unit configured to obtain information relating to a posture of an imaging device that is imaging a region of a subject, and a determination unit configured to perform a determination, based on the information relating to the posture, regarding which region of the subject corresponds to the region imaged by the imaging device.

Further features of the present invention will become apparent from the following description of exemplary embodiments (with reference to the attached drawings).

DESCRIPTION OF THE EMBODIMENTS

Below, with reference to the attached drawings, a detailed description is given for the present invention based on embodiments. Note that configurations illustrated in the following embodiments are merely examples, and the present invention is not limited to the illustrated configurations.

First Embodiment

An information processing apparatus in a first embodiment determines an imaged region of a subject based on a tally value for posture information of an imaging device. In the present embodiment, the imaging device is an ultrasonic probe in an ultrasonic diagnosis apparatus, and below a description is given of the ultrasonic probe as something for imaging a specific region (for example, a breast) of a subject, and discriminating to which of left and right objects an imaged region corresponds (if the imaged region is a breast, whether the breast is on the left or right of the chest).

Figure 1:
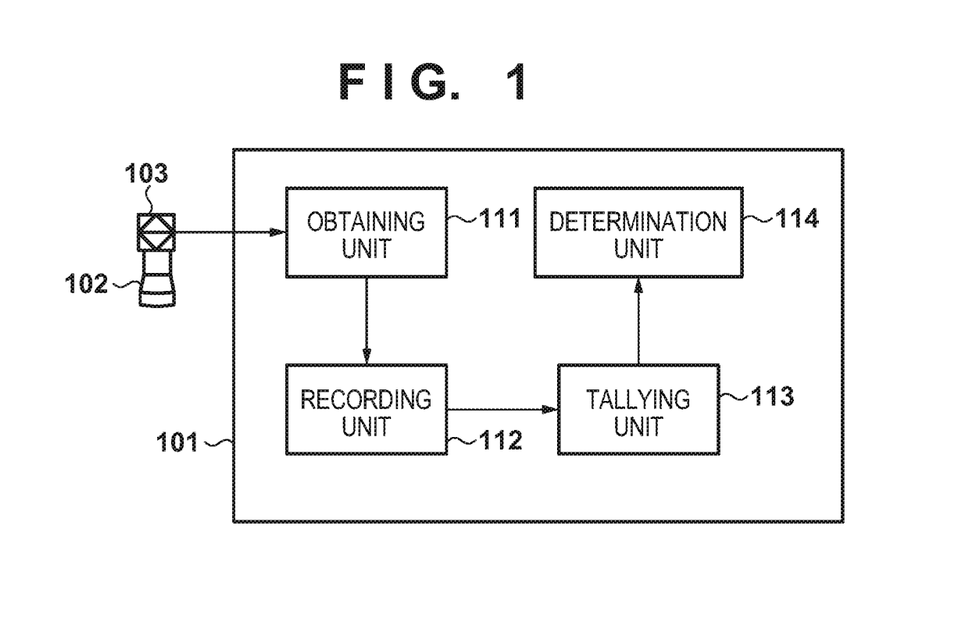
FIG. 1 illustrates a functional configuration of an information processing apparatus in a first embodiment.

FIG. 1 is a view illustrating an example of a functional configuration of an information processing apparatus 101 in the first embodiment. An obtaining unit 111 obtains information (hereafter, posture information) representing a state such as an inclination or a direction of an imaging device (for example, an ultrasonic probe) 102 that is measured by a posture sensor 103. For example, the obtaining unit 111 obtains, as the posture information, information regarding an inclination (pitch or roll) of the imaging device 102 with respect to a left-and-right direction and a cranio-caudal direction, as described below with reference to FIG. 3. In the present embodiment, the information regarding the inclination of an imaging device is information of an inclination angle. However, limitation is not made to this, and the obtaining unit 111 may obtain, as the posture information, binary values indicating whether inclination angles in the cranio-caudal direction and the left-and-right direction of the imaging device 102 are positive or negative. The posture information of the imaging device 102 (information of an inclination angle in the present embodiment) is obtained by attaching to the imaging device 102 various sensors such as a gyro sensor, a position posture sensor, and an inclination sensor, for example, as the posture sensor 103. Note that there is not necessarily a need for integration, and, in a case when the imaging device 102 is gripped and operated by an operator, the various sensors may be, for example, attached to an arm or a hand of the operator instead of being attached to the imaging device 102.

A recording unit 112 successively records posture information successively obtained by the obtaining unit 111 in a storage device 203 that is described later. A tallying unit 113 performs a tally of information recorded in the storage device 203 by the recording unit 112. A determination unit 114 performs a determination of whether a region imaged by the imaging device 102 is on the left or right of a chest, based on the information tallied by the tallying unit 113. The determination unit 114 can generate, based on a determination result, information for presenting to an operator as an imaged region determination processing result, and performs display control for outputting (displaying) the imaged region determination processing result via an output device 205 (FIG. 2).

Figure 2:
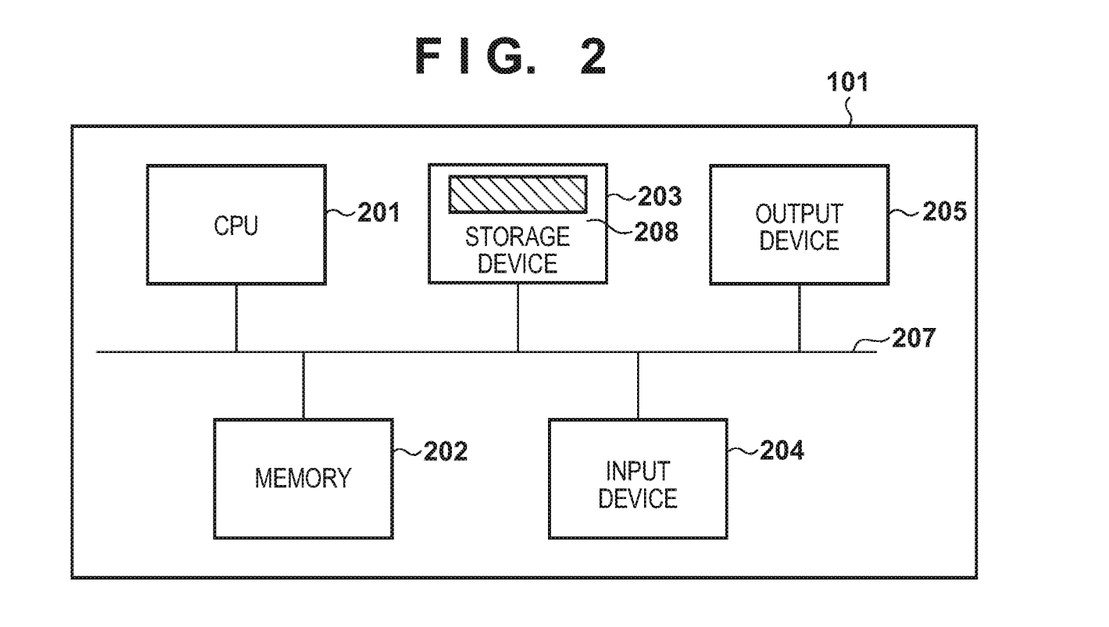
FIG. 2 illustrates an example of a hardware configuration of the information processing apparatus in embodiments of the present invention.

FIG. 2 is a view illustrating an example of a hardware configuration of the information processing apparatus 101 in the present embodiment. The information processing apparatus 101 is provided with a CPU (Central Processing Unit) 201, a memory 202, the storage device 203, and an input device 204, and these are mutually connected by a bus 207.

The CPU 201 executes various functions that are described later by executing a program 208 stored in the storage device 203. The memory 202 temporarily stores data or a program read from the storage device 203 by the CPU 201. In addition, the memory 202 is also used as a region for the CPU 201 to execute various programs.

The storage device 203 stores an operating system (OS), various programs, a control program, data, or the like. Note that the program 208, which is for control is stored as some of the data of the storage device 203. Computational processing, such as tallying posture information, the imaged region determination processing that is performed from the computation result, or the like, may be given as a program. Functions or processing of the information processing apparatus 101 can be realized by the CPU 201 reading a program stored in the storage device 203, and executing this program.

The input device 204 accepts, by way of input by an operator, or the like, an instruction for obtaining posture information of the imaging device 102, and an instruction such as for starting or stopping imaging that is made with respect to the imaging device 102.

The output device 205 functions as a display unit, for example, and outputs (displays) an imaged region determination processing result that is generated by the determination unit 114 based on the posture information of the imaging device 102.

Figure 3:
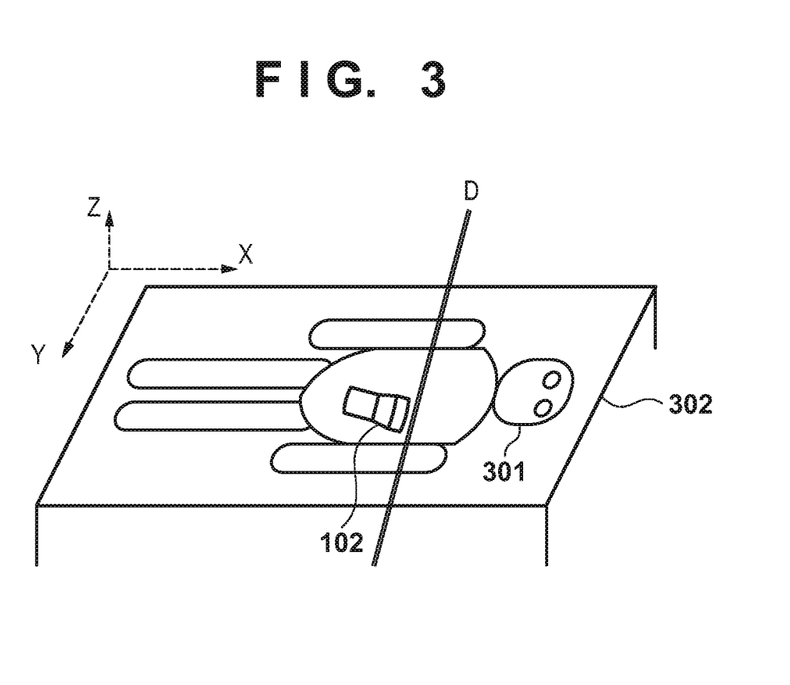
FIG. 3 is a view for describing an example of an imaging environment in the first embodiment.

FIG. 3 is a view for illustrating an example of an imaging environment in a case when the imaging device 102 is used to perform imaging. In the imaging environment illustrated in FIG. 3, a subject 301 is lying in a supine position on a bed 302, and, for example, an operator performs imaging by applying the imaging device 102 to the subject 301. At this point, it is assumed that imaging is performed by the imaging device 102 for only one side of the chest that has left and right sides.

As an imaging space, an apparatus coordinate system 303 in which an X axis is a cranio-caudal direction of the subject on the bed 302 (with a cranial side as positive), a Y axis is a left-and-right direction that crosses the subject on the bed 302 (with a right side of the subject 301 lying in the supine position seen from a foot side as positive), and a Z axis is a vertical direction with respect to a bed surface (with an upward side from the subject 301 lying in the supine position as positive) is defined. Note that the posture information of the imaging device 102 is, for example, defined in accordance with an inclination of a vertical axis of a non-illustrated imaging plane of the imaging device 102, and is measured by the posture sensor 103 in the apparatus coordinate system 303. For example, when the imaging device 102 is inclined in a positive direction for the Y axis (the left-right axis) with respect to the Z axis (the vertical axis) of the apparatus coordinate system 303, the posture sensor 103 records the inclination angle as a "positive value in the left-and-right direction", and, when the imaging device 102 is inclined in a negative direction for the Y axis, the posture sensor 103 records the inclination angle as a "negative value for the left-and-right direction". Similarly, for example, when the imaging device 102 is inclined in a positive direction for the X axis (the cranio-caudal axis) with respect to the Z axis, the posture sensor 103 records the inclination angle as a positive value in the cranio-caudal direction, and the reverse is recorded as a negative value. In the description below, a description is given based on the apparatus coordinate system 303 described above. Note that, typically, an inclination angle is defined with respect to a gravity axis because the bed surface is horizontal, but a configuration may be taken to measure an inclination angle with respect to the bed surface when the bed surface is inclined with respect to the horizontal plane.

Figure 4:
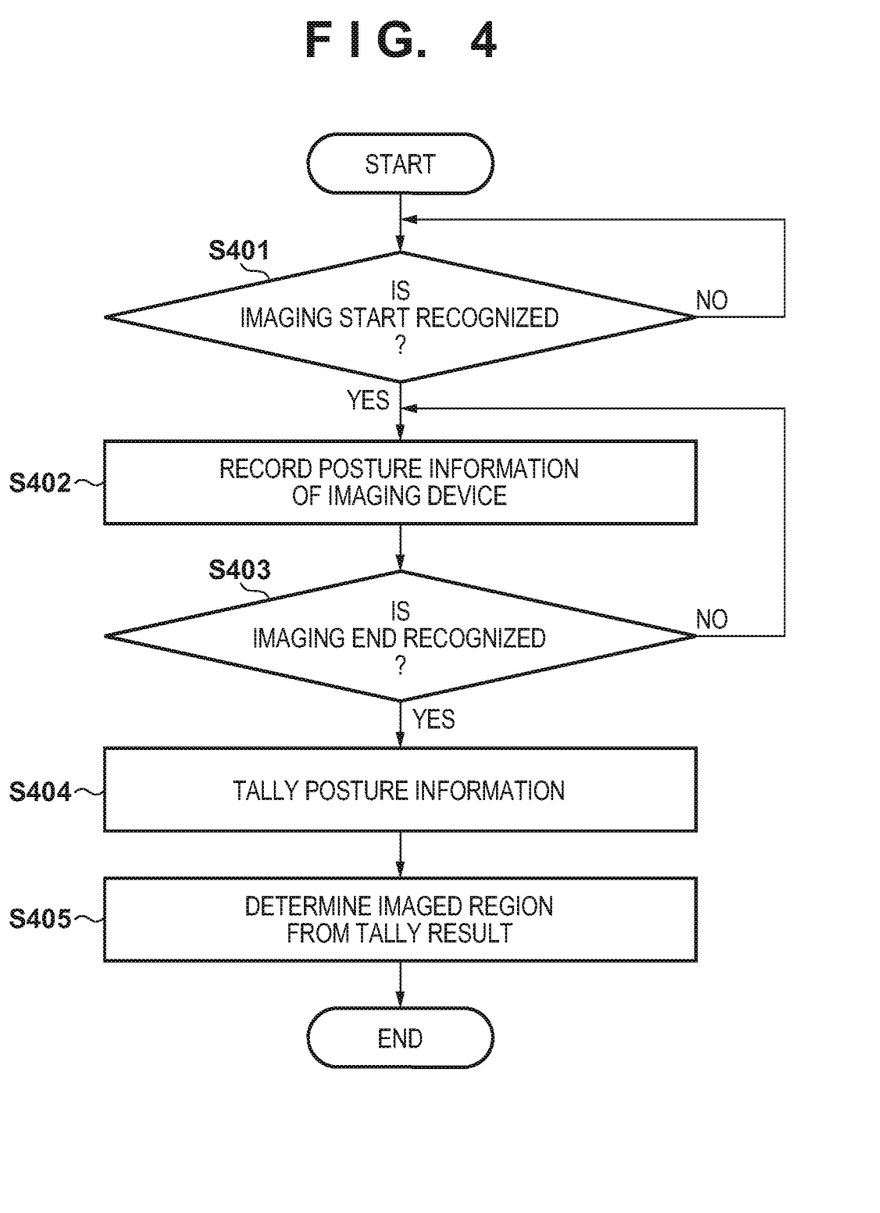
FIG. 4 is a flowchart for illustrating processing by the information processing apparatus in the first embodiment.

FIG. 4 is a flowchart illustrating imaged region determination processing by the information processing apparatus 101. In step S401, upon recognizing a start of imaging by the imaging device 102 (Yes in step S401), the obtaining unit 111 starts obtaining posture information of the imaging device 102, and the processing advances to step S402. For example, in response to an imaging start button (not shown) equipped by the imaging device 102 being operated by an operator, the obtaining unit 111 recognizes imaging by the imaging device 102, and, subsequently, in response to an operator performing an instruction with respect to the input device 204 for obtaining posture information of the imaging device 102, the obtaining unit 111 starts obtainment of the posture information of the imaging device 102. In addition, for example, after an operator has performed an instruction to the input device 204 for obtaining the posture information of the imaging device 102, the obtaining unit may start obtainment of the posture information of the imaging device 102 at a time when the imaging device 102 touched the subject 301. Note that, as described above, in the present embodiment, the posture information of the imaging device 102 is an inclination angle in the apparatus coordinate system 303 of the imaging device 102. Meanwhile, processing waits until the obtaining unit 111 recognizes a start of imaging by the imaging device 102 (No in step S401).

In step S402, the recording unit 112 stores in the storage device 203 posture information (an inclination angle in the present embodiment) of the imaging device 102 that is successively measured by the posture sensor 103 and obtained by the obtaining unit 111. Here, with reference to FIG. 5, a description is given regarding an inclination angle of the imaging device 102.

Figure 5:
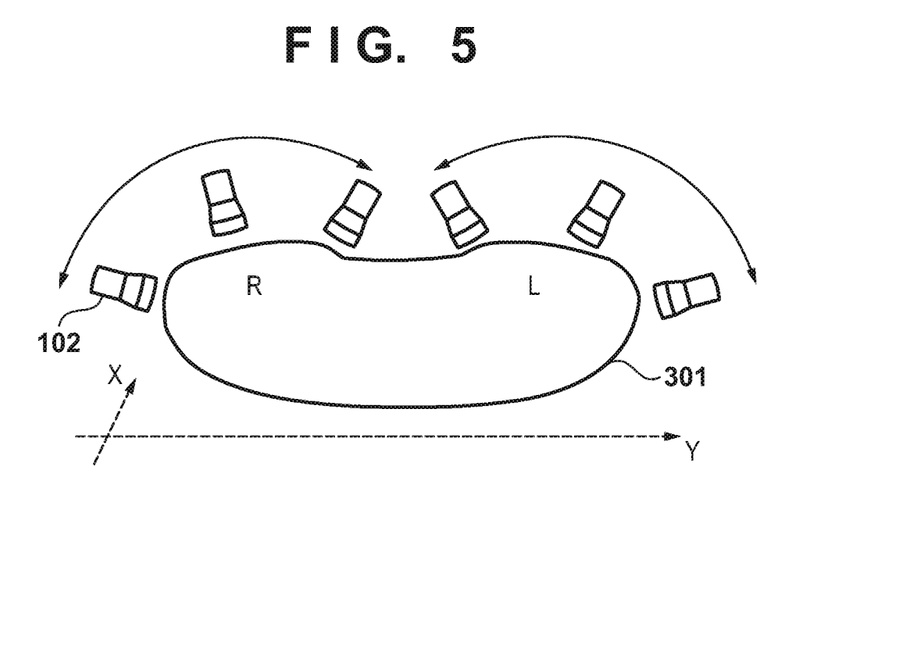
FIG. 5 is a view for exemplifying movement of an imaging device when imaging a subject.

FIG. 5 is a view for exemplifying motion of the imaging device 102 that is imaging the subject 301. The subject 301 in FIG. 5 indicates an image where a cross section of the subject 301 at a line indicated by reference symbol D in FIG. 3 is seen from a foot side of the subject 301. An operator applies the imaging device 102 following a body surface of one side (a left side or a right side) of the chest of the subject 301. Here, a case when the operator applies the imaging device 102 to a left side (an L side) of the chest illustrated in FIG. 5, in other words a case when a left breast of the subject is imaged, for example, is considered. In such a case, when the imaging device 102 is positioned near a center of the chest (near the sternum), an inclination angle in the left-and-right direction is a small negative value. As the position of the imaging device 102 is directed from near the center of the chest to outside (near a body side portion), the inclination of the imaging device increases, and, thus, the inclination angle in the left-and-right direction becomes a large positive value. Conversely, a case when the operator applies the imaging device 102 to a right side (an R side) of the chest, in other words a case when a right breast is imaged, for example, is considered. In such a case, the inclination angle in the left-and-right direction when the imaging device 102 is positioned near the center of the chest is a small positive value, and becomes a large negative value as the imaging device 102 is directed to the side of the body.

Returning to FIG. 4, in step S403, upon recognizing an end of imaging by the imaging device 102 (Yes in step S403), the obtaining unit 111 ends obtaining of posture information by the imaging device 102, and the processing advances to step S404. For example, the obtaining unit 111 may recognize an end of imaging by the imaging device 102 when an end of obtainment of the posture information of the imaging device 102 is instructed in accordance with an instruction by an operator via the input device 204. For example, a configuration may be taken such that, in response to an imaging end button (not shown) equipped by the imaging device 102 being operated by an operator, the obtaining unit 111 recognizes an end of imaging by the imaging device 102. Meanwhile, the obtaining unit 111 continues the processing of step S402 until the end of the imaging by the imaging device 102 is recognized (No in step S403). In addition, if a configuration is such that the obtaining unit 111 and the imaging device 102 operate in coordination, the obtaining unit 111 may continue obtaining the posture information of the imaging device 102 while the imaging device 102 is performing imaging.

In step S404, the tallying unit 113 performs a tally calculation for the plurality of pieces of posture information recorded in the storage device 203 by the recording unit 112 in step S403. For example, the tallying unit 113 tallies the posture information of the imaging device 102 stored in the storage device 203 to generate distribution information of the posture information as a tally result. In the present embodiment, as an example, the tallying unit 113 identifies a range (in other words, a maximum value and a minimum value) of the inclination angle in the left-and-right direction recorded by the recording unit 112, and generates this range as the distribution information. Here, with reference to FIGS. 6A and 6B, a description is given regarding the distribution information of the inclination angle as the posture information generated by the tallying unit 113.

Figure 6A:
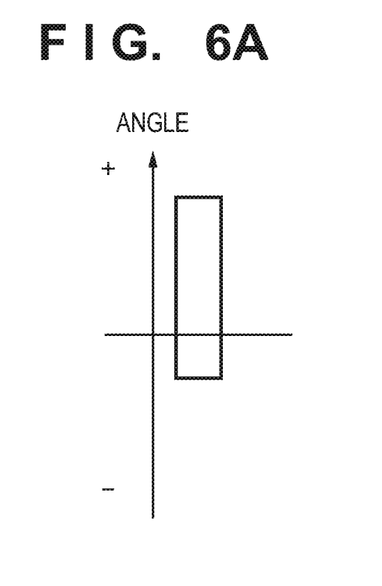
FIGS. 6A and 6B are views for illustrating examples of tally results for posture information in the first embodiment.
Figure 6B:
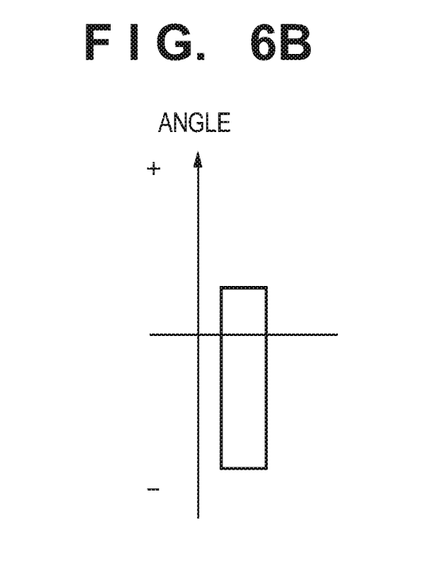

FIGS. 6A and 6B illustrate an example of a tally result of the posture information generated by the tallying unit 113 (in other words, distribution information of the inclination angle). FIG. 6A illustrates an example of distribution information of an inclination angle with respect to the left-and-right direction for when the imaging device 102 is applied to the left side (L side) of the chest illustrated by FIG. 5. In addition, FIG. 6B illustrates an example of distribution information of an inclination angle with respect to the left-and-right direction for when the imaging device 102 is applied to the right side (R side) of the chest illustrated by FIG. 5. Note that FIGS. 6A and 6B illustrate maximum values and minimum values for the inclination angle in the left-and-right direction as the distribution information of the inclination angle, but the tallying unit 113 may generate an average value or a median value of the inclination angle in the left-and-right direction as the distribution information of the inclination angle. In addition, the tallying unit 113 may generate a histogram of the inclination angle in the left-and-right direction as the distribution information of the inclination angle.

Returning to FIG. 4, in step S405, the determination unit 114 determines whether the region imaged by the imaging device 102 (imaged region) is on the left or right of the chest, based on the tally result generated in step S404. For example, the determination unit 114 may perform the determination in accordance with a maximum value of the inclination angle of the imaging device 102. Here, when imaging the left side of the chest (for example, a left breast), there are cases when the imaging device 102 is inclined so as to follow a body side portion on the left side, and, thus, a maximum value of the inclination angle in the left-and-right direction is a large value. In contrast, when imaging the right side of the chest (for example, a right breast), greatly inclining the imaging device 102 on the left side does not occur, and, thus, a maximum value of the inclination angle in the left-and-right direction is a small value. Accordingly, the determination unit 114 can determine that the imaged region is a left side when a maximum value of the inclination angle in the left-and-right direction is greater than a predetermined threshold value, and determine that the imaged region is a right side in other cases.

Note that the determination unit 114 may determine the imaged region to be a left side if an average value or median value of the inclination angle in the left-and-right direction is positive, and determine the imaged region to be the right side if this average value or median value is negative. In addition, the determination unit 114 may determine left or right for the imaged region based on a value that combines a plurality of values (for example, an average value, or the like, of a maximum value and a minimum value), instead of a single value. In addition, in a case of tallying by a histogram, the determination unit 114 may determine left or right for an imaged region based on an inclination angle in the left-and-right direction where a frequency in the histogram is greatest, or a ratio of positive/negative for inclination angles in the left-and-right direction. In addition, the determination unit 114 may fit a predetermined distribution model (for example, a normal distribution model) to the histogram, and determine left or right for an imaged region based on an inclination angle in the left-and-right direction at a center.

By the description above, the information processing apparatus in the first embodiment can easily determine the imaged region of a subject based on a tally value of posture information of an imaging device.

(First Variation of First Embodiment)

In the first embodiment, a description was given of a case of determining, based on the inclination angle of the imaging device 102, whether imaging was performed on the left side or the right side of a chest (for example, a right breast or a left breast), as an example. However, there is no limitation to the chest, and any region may be taken if it is possible to use the inclination angle of the imaging device 102 at the time of imaging to determine to which region of a subject an imaged region corresponds. For example, the method indicated in the first embodiment may be applied to a left-right determination such as for a head, a cheek, or a buttock, or a left-right up-down determination for an abdomen. In addition, regardless of the region, in a case of, when the subject has a lateral position posture, imaging from the abdomen to the waist or over the back around the abdomen, it is possible to determine whether there is an image of an abdomen side or an image of a back side by applying the method indicated in the first embodiment. In addition, the subject is not limited to a human body and an application range such as an animal or a device may be employed.

(Second Variation of First Embodiment)

Figure 7:
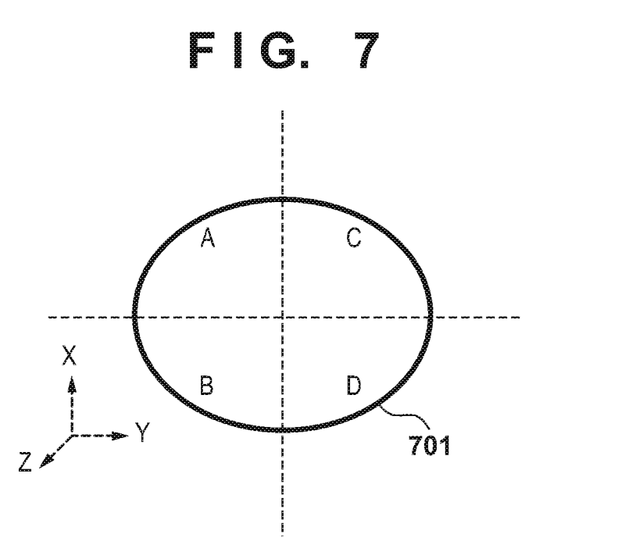
FIG. 7 is a view for giving a description regarding an imaged region for which a determination is made, in a variation of the first embodiment.
Figure 8:
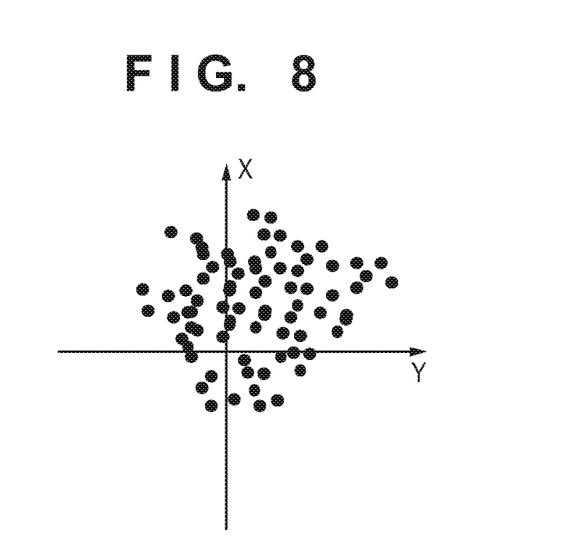
FIG. 8 is a view for illustrating an example of a tally result of posture information in a variation of the first embodiment.

The first embodiment was an example of discriminating an imaged region by using the inclination angle information of one dimension, the left-and-right direction. However, it is possible to discriminate an imaged region by using inclination angle information of two dimensions or more (one or more directions), such as the left-and-right direction and the cranio-caudal direction. For example, if it is known which of left and right breasts an imaging target is, it is possible to determine what region of the breast is imaged in accordance with the inclination angle of the imaging device 102 at a time of imaging. FIG. 7 is a view for giving a description regarding an imaged region determined in the present variation. In FIG. 7, A, B, C, and D regions in a left breast 701 are illustrated. An example of a tally result (in other words, distribution information of an inclination angle) of posture information of the imaging device 102 that performed imaging with respect to this breast is illustrated in FIG. 8. In FIG. 8, inclination angles in the left-and-right direction and the cranio-caudal direction for the inclination angle of the imaging device 102 are plotted.

Referring to FIG. 7 and FIG. 8, it is understood that, in a case of imaging an upward side with respect to the breast 701 (the A and C regions) the inclination angle of the imaging device 102 is a value on the positive side of the X axis (the cranio-caudal direction), and, in a case of imaging the left side (the C and D regions), the inclination angle of the imaging device 102 takes a value on the positive side of the Y axis (the left-and-right direction). Similarly, it is understood that the inclination angle takes a value on the negative side of the X axis when imaging a downward side (the B and D regions), and the inclination angle takes a value on the negative side of the Y axis when imaging the right side (the A and B side). From these tendencies, the determination unit 114 can determine which region is imaged by the imaging device 102. For example, the determination unit 114 can determine which region an imaged region is in accordance with which quadrant has the most plotting. In the case of the example of FIG. 8, because most plots are made for positive values for both X and Y, the determination unit 114 can determine that the imaged region was the C region.

Figure 9:
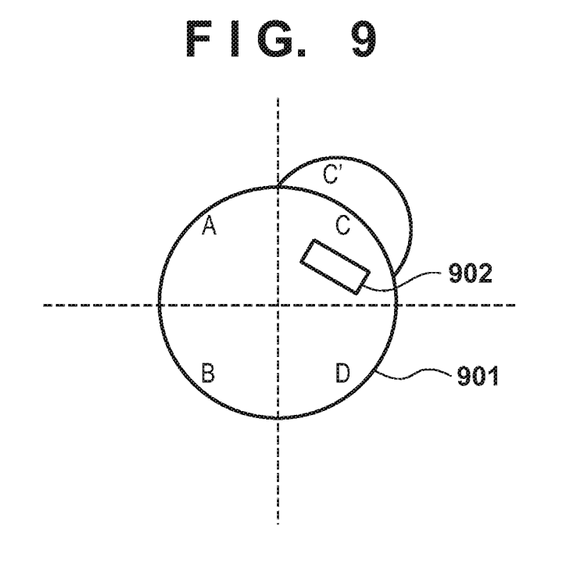
FIG. 9 is a view for giving a description regarding an example of a display based on an imaged region determination result in a variation of the first embodiment.

FIG. 9 illustrates an imaged region determination processing result that is created by the determination unit 114 based on a tally result as in FIG. 8, and is outputted (displayed) by the output device 205. In FIG. 9, a probe mark is overlapped at a position in the region corresponding to a body mark and displayed. In addition, because a rotation angle of the imaging device 102 is measured by the posture sensor 103 during imaging, a probe mark 902 that represents a rotation angle measured most is also displayed in the C region.

Second Embodiment

In the first embodiment, a description was given regarding an example of a case of determining an imaged region based on a tally value of posture information when one time of (one continuity) imaging was performed with respect to the left side or the right side of a subject. In contrast to this, in the present embodiment, a description is given regarding an example of a case of more reliably and easily determining an imaged region based on a tally value of posture information in a plurality of times of imaging with respect to a left side or a right side of a subject. A description is given below regarding a case of automatically determining, based on a predetermined condition, switching between imaging of a left side of a subject and imaging of a right side.

Figure 10:
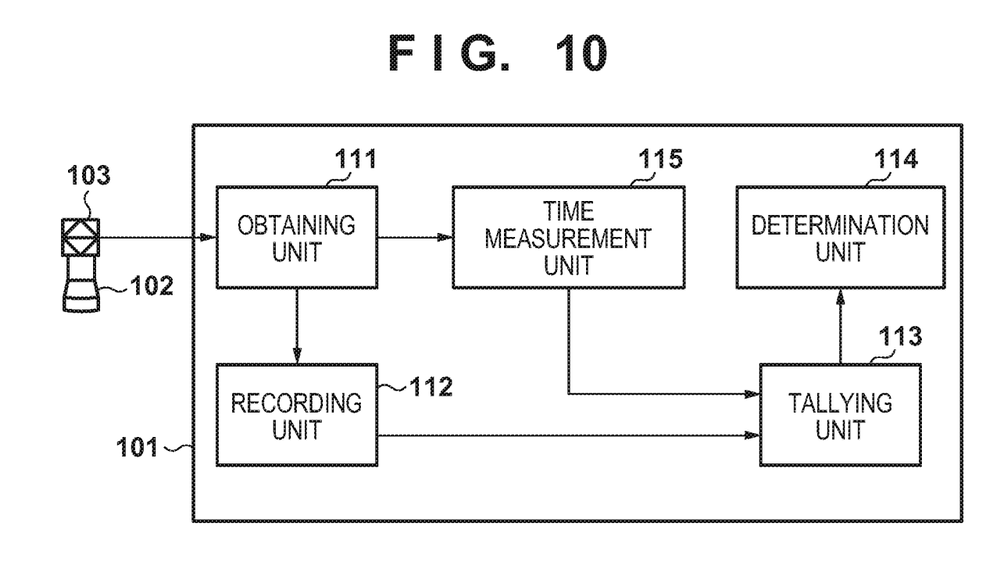
FIG. 10 illustrates a functional configuration of an information processing apparatus in a second embodiment.

FIG. 10 is a view illustrating an example of a functional configuration of the information processing apparatus 101 in the second embodiment. Description of functionality common with that of FIG. 1 described in the first embodiment is omitted. A time measurement unit 115 measures a length of an amount of time in which the imaging device 102 is not imaging. The tallying unit 113 performs tallying of the information recorded in the storage device 203 by the recording unit 112 until the amount of time measured by the time measurement unit 115 becomes larger than a predetermined value.

Figure 11:
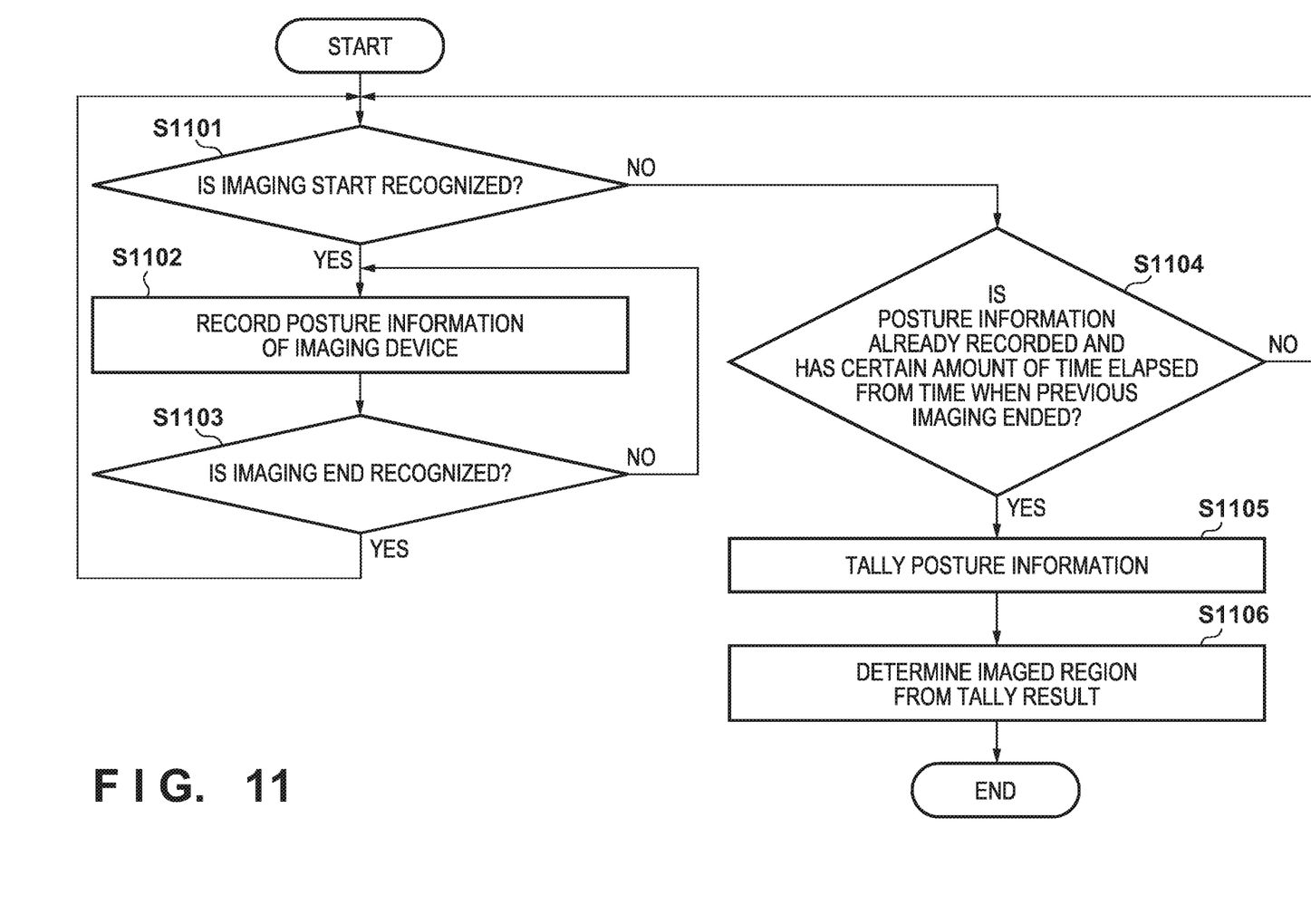
FIG. 11 is a flowchart for illustrating processing by the information processing apparatus in the second embodiment.

FIG. 11 is a flowchart for illustrating imaged region determination processing by the information processing apparatus 101 in the second embodiment. In step S1101, upon recognizing a start of imaging by the imaging device 102 (Yes in step S1101), the obtaining unit 111 starts obtaining posture information of the imaging device 102, and the processing advances to step S1102. Because regarding recognition of imaging start is the same as in step S401 of FIG. 4, which is described in the first embodiment, a description is omitted. Meanwhile, when the obtaining unit 111 could not recognize a start of imaging (No in step S1101), the processing advances to step S1104.

Because the processing of step S1102 is the same as the processing of step S402 of FIG. 4, which is described in the first embodiment, a description is omitted.

In step S1103, when the obtaining unit 111 recognizes the end of imaging by the imaging device 102 (Yes in step S1103), the processing returns to step S1101 and repeats. Because regarding recognition of an imaging end is the same as in step S403 of FIG. 4, which is described in the first embodiment, a description is omitted. In addition, when the obtaining unit 111 could not recognize an end of imaging (No in step S1103), the processing of step S1102 continues.

In step S1104, the tallying unit 113 determines whether a condition such as that the posture information of the imaging device 102 has already been stored in the storage device 203 by the recording unit 112 and a certain amount of time has elapsed, since imaging of a previous time has ended, is satisfied. In the first embodiment, as described with reference to FIG. 3, it is often the case that, until imaging of one side of a chest completes, imaging is performed consecutively without opening much time. In other words, it is often the case that, with respect to a chest that has left and right sides, until imaging of one side of the chest completes, switching to imaging of the opposite side is not performed. Accordingly, for imaging with respect to one side of a chest that has left and right sides, there is a tendency for a time interval after one continuity of imaging finishes until the next imaging is started to be short. In contrast, in a case of switching to imaging of the opposite side of a chest after imaging of one side of the chest completes, there is a tendency for a time interval from when a continuity of imaging with respect to one side of a chest ends until imaging with respect to the other side of the chest is started to be long. Accordingly, the tallying unit 113 can determine, in accordance with a time interval, whether an imaged region has switched from one side of a chest to the other side.

Considering such a background, when the foregoing condition is satisfied (Yes in step S1104), the tallying unit 113 determines that imaging of one side is complete, and the processing advances to step S1105. Meanwhile, when the foregoing condition is not satisfied (No in step S1104), the processing returns to step S1101 and repeats.

In step S1105, the tallying unit 113 performs a tallying calculation of the posture information recorded in the storage device 203 in step S1103. For example, the tallying unit 113 tallies an inclination angle of the imaging device 102 stored in the storage device 203 to generate distribution information of the inclination angle as a tally result for posture information.

Figure 12:
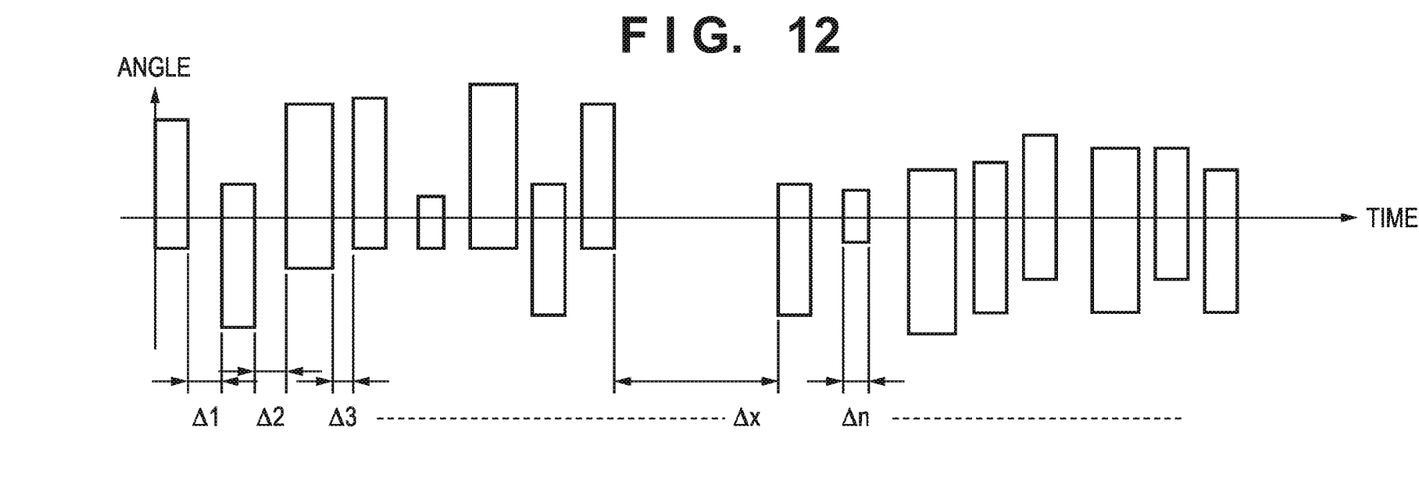
FIG. 12 is a view for giving a description regarding a record of an inclination angle in the second embodiment.

FIG. 12 illustrates an example of a tally result of the posture information tallied by the tallying unit 113 (in other words, distribution information of the inclination angle). In FIG. 12, taking the ordinate is an inclination angle and the abscissa as time, a range for the inclination angle obtained by one time of (a continuity of) imaging is represented by strip shapes. One strip signifies one time of imaging from start to end, and an interval between strips represents a time interval A from the end of imaging until the start of subsequent imaging.

Next, in step S1106, the determination unit 114 determines whether the region imaged by the imaging device 102 (imaged region) is on the left or right of the chest, based on the tally result generated in step S404. In the present embodiment, it is assumed that the determination unit 114 determines whether an imaged region is on the left or right side of a chest based on a number of times that the inclination angle exceeds a predetermined angle.

For example, when the inclination angle has exceeded a predetermined angle (for example, positive eighty degrees) a predetermined number of times (for example, three times) or more, the determination unit 114 determines that the imaged region is on the left side. Alternatively, the determination unit 114 may determines whether the imaged region is on the left or the right side of the chest based on a ratio of the number of times the inclination angle exceeds the predetermined angle with respect to the total number of times of imaging. In such a case, for example, the determination unit 114 may obtain a number of times of imaging from the time intervals A of FIG. 12, and determine the imaged region to be the left side when the number of times of imaging where the inclination angle exceeds the predetermines angle exceeds a predetermined ratio (for example, 30%). Limitation is not made to this, and similar to the first embodiment, the determination unit 114 may determine whether the imaged region is on the left or right side of the chest based on a single value such as a maximum value, a median value, or an average value of the inclination angle of the imaging device 102, or a value obtained by combining a plurality of values. In addition, the determination unit 114 may discriminate whether there are more positive or negative left/right inclination angles in each imaging (whether the imaging tends to be done at more positive angles or tends to be done at more negative angles), and determine the imaged region to be the left side when the number of imagings that tend positive is greater, and determine the imaged region to be the right side when the number of imagings that tend negative is greater. Note that, at this point, for an imaging event when the positive/negative ratio in one imaging does not exceed a predetermined ratio, this may be removed from the foregoing tally as an imaging event for which discrimination of tending positive or tending negative would be difficult. Consequently, discriminating right and left with higher accuracy is possible by removing unclear information.

By the description above, the information processing apparatus in the second embodiment can provide a mechanism for more reliably and easily determining the imaged region of a subject based on a tally value of posture information of an imaging device in a plurality of imagings.

Third Embodiment

In the first embodiment and the second embodiment, a description was given of examples of cases when an imaged region is determined after tallying an inclination angle after the completion of imaging. In the present embodiment, a description is given of an example of a case of determining an imaged region before imaging and during imaging.

Figure 13:
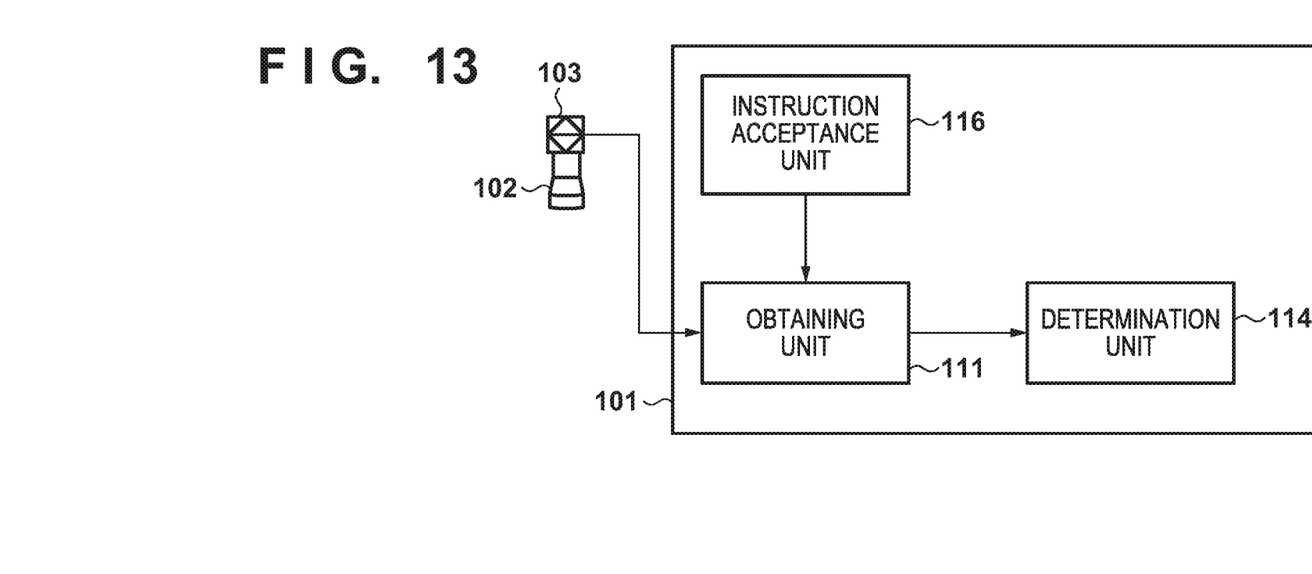
FIG. 13 illustrates a functional configuration of an information processing apparatus in a third embodiment.

FIG. 13 is a view illustrating an example of a functional configuration of the information processing apparatus 101 in the third embodiment. A description of functionality common with FIG. 1 is omitted. An instruction acceptance unit 116 notifies the obtaining unit 111 of a timing when an instruction from an operator via the input device 204 is accepted. The obtaining unit 111 obtains the inclination angle of the imaging device 102 at the timing notified from the instruction acceptance unit 116, and the determination unit 114 determines to which region of the subject the imaged region corresponds, based on the inclination angle of the imaging device at that timing (if the imaged region is the chest, determines whether the imaged region is the left side or the right side of the chest).

A description is given of an example of using the information processing apparatus 101 in the present embodiment. Before imaging, an operator tilts the imaging device 102 and then provides a determination instruction to the instruction acceptance unit 116 via the input device 204 (a button, a GUI, or the like, in the present embodiment). In addition, the instruction acceptance unit 116 may determine that a determination instruction has been received when an operator operates the imaging device 102 by a posture that satisfies a predetermined condition (for example, when the inclination angle of the imaging device 102 is greater than or equal to a predetermined angle) or when the imaging device 102 has been stationary for a predetermined amount of time or more at a predetermined angle or more.

The determination unit 114 of the information processing apparatus 101 in the present embodiment determines the imaged region based on the posture (the inclination angle) of the imaging device 102 at the timing when the instruction acceptance unit 116 accepted the determination instruction. For example, in a case of performing imaging of the left side of a chest, an operator provides a determination instruction to the instruction acceptance unit 116 after, before imaging, tilting the imaging device 102 toward the positive direction of the Y axis (left and right axis) with respect to the Z axis (driving axis). In a case of performing imaging of the right side of the chest, the operator performs a similar operation after tilting the imaging device 102 toward the negative direction. The determination unit 114 determines whether the imaged region is the left or right side of the chest in accordance with whether the inclination angle of the imaging device 102 at the timing when the determination instruction was provided is positive or negative. In order to avoid erroneous determination, a condition such as determining when the inclination angle is greater than or equal to positive thirty degrees or less than or equal to negative thirty degrees may be provided. In addition, there is no limitation to before imaging, and a configuration may be taken to perform determination processing after a clear determination instruction is provided during imaging or after imaging.

As described above, the information processing apparatus in the third embodiment can provide a mechanism for easily determining the imaged region of a subject without being limited to after imaging.

Fourth Embodiment

In the present embodiment, a description is given regarding operation of an ultrasonic diagnosis apparatus equipped with the information processing apparatus 101, the imaging device 102, and the posture sensor 103, which are described in the above embodiments. A hardware configuration of the ultrasonic diagnosis apparatus is similar to that shown in FIG. 2, which is described in the first embodiment. Note that, in the present embodiment, it is assumed that a monitor is used as the output device 205.

Figure 14:
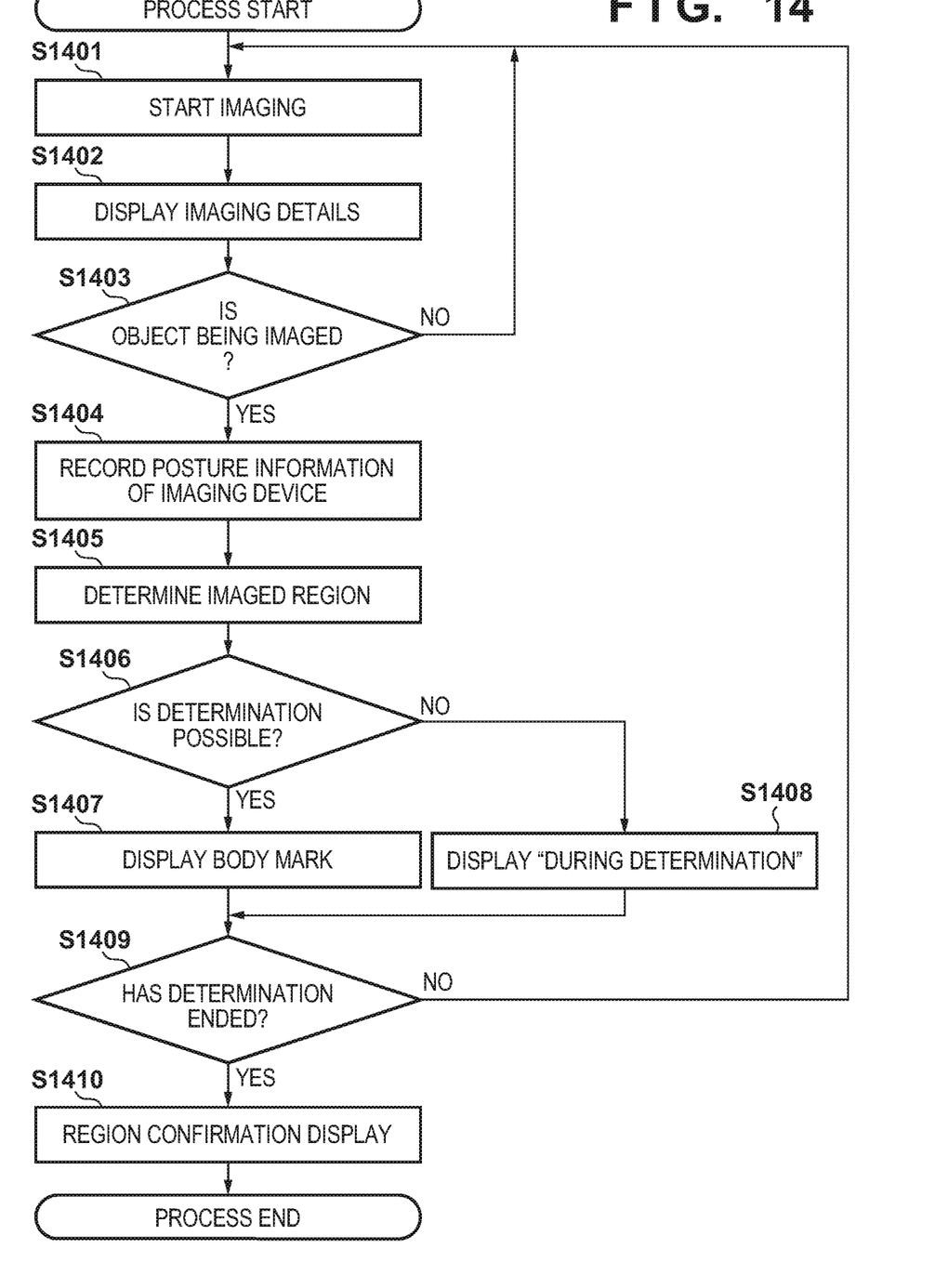
FIG. 14 is a flowchart for illustrating processing by an ultrasonic diagnosis apparatus in a fourth embodiment.

FIG. 14 is a flowchart for illustrating processing performed by an ultrasonic diagnosis apparatus in a fourth embodiment. In step S1401, the ultrasonic diagnosis apparatus starts imaging an ultrasonic tomogram by the imaging device 102. In step S1402, the ultrasonic diagnosis apparatus displays the ultrasonic tomogram imaged in step S1401 on a monitor (the output device 205).

In step S1403, the ultrasonic diagnosis apparatus starts determining whether the imaging device 102 is imaging a subject. Because a determination method is similar to that of the first embodiment (step S401 of FIG. 4), a description thereof is omitted. In a case of imaging a subject (Yes in step S1403), the processing advances to step S1404. Meanwhile, when imaging is not being performed (No in step S1403), the processing returns to step S1401 and repeats. In step S1404, the ultrasonic diagnosis apparatus records in the storage device 203 posture information (for example, an inclination angle) of the imaging device 102 that is measured by the posture sensor 103.

In step S1405, the ultrasonic diagnosis apparatus determines whether it is possible to execute a determination of a region from the posture information recorded thus far. For example, in a case when a number of measurements of an inclination angle as posture information has not exceeded a predetermined value, as with immediately after starting imaging of a subject, the ultrasonic diagnosis apparatus determines that a determination of the region is impossible. In a case of determining to perform a determination of the region, the ultrasonic diagnosis apparatus determines the imaged region based on a plurality of pieces of posture information recorded by that time. This determination method is similar to that in the first or second embodiment (step S405 of FIG. 4 or step S1106 of FIG. 11). However, a point of determining based on measurement up to the current time from the start of imaging a subject differs from the embodiments described above. Here, for example, if the inclination angle in the left-and-right direction does not show characteristic distribution in either the positive side or the negative side, the ultrasonic diagnosis apparatus determines that a determination of the region is impossible.

In step S1406, the ultrasonic diagnosis apparatus confirms whether the imaged region was able to be determined by the processing of step S1405. When an imaged region was able to be determined (Yes in step S1406), the processing advances to step S1407. Meanwhile, when an imaged region was not able to be determined (No in step S1406), the processing advances to step S1408.

In step S1407, the ultrasonic diagnosis apparatus displays information based on the determined left or right information on the monitor (the output device 205). For example, if a measurement target is a breast, the ultrasonic diagnosis apparatus arranges and displays an ultrasonic image with a body mark on whichever left or right side was discriminated. Note that, regarding a display position, a display form such as an overlay display or a case of displaying on a specific display area may be used. In step S1408, the ultrasonic diagnosis apparatus displays, for example, "determining", "unknown", or the like, on a monitor (the output device 205) in order to indicate a state where determination of the imaged region could not be performed.

In step S1409, the ultrasonic diagnosis apparatus confirms whether imaging has ended. When imaging ends (Yes in step S1409), the processing advances to step S1410. In a case of continuing imaging (No in step S1409), the processing returns to step S1401 and the processing repeats. In step S1410, the ultrasonic diagnosis apparatus displays the region that was imaged and determined on the monitor (the output device 205). This is for an operator to check for misrecognition or non-recognition of the imaged region, and the operator makes a correction or inputs the imaged region as necessary.

As described above, the ultrasonic diagnosis apparatus in the fourth embodiment can determine and display an imaged region of a subject during imaging.

A description in detail was given above for the embodiments of the present invention, but the present invention is not limited to these specific embodiments, and various variations or changes are possible in the scope of the spirit of the present invention recited in the scope of the claims.

Other Embodiments

Embodiment(s) of the present invention can also be realized by a computer of a system or an apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., an application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., a central processing unit (CPU), or a micro processing unit (MPU)) and may include a network of separate computers or separate processors to read out and to execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), a digital versatile disc (DVD), or a Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

What is claimed is:

1. An information processing apparatus comprising:
a memory storing a program; and
one or more processors that, by executing the program, function as:
   (a) an obtaining unit configured to obtain information relating to an inclination angle of an imaging device that is imaging a region of a subject;
   (b) a determination unit configured to perform a determination, based on the information relating to the inclination angle of the imaging device, regarding which region of the subject corresponds to the region imaged by the imaging device, wherein the determination unit performs the determination based on the information relating to the inclination angle obtained at a timing when the inclination angle of the imaging device satisfies a predetermined angle condition; and
   (c) a tallying unit configured to generate a tally result by tallying information relating to a plurality of inclination angles of the imaging device obtained by the obtaining unit,
wherein the determination unit performs the determination based on the tally result generated by the tallying unit, and
wherein the tallying unit tallies the information relating to the inclination angle of the imaging device obtained by the obtaining unit at a time when one continuous imaging by the imaging device ends.

2. The information processing apparatus according to claim 1, wherein the tallying unit generates information indicating a distribution of inclination angles of the imaging device as the tally result.

3. The information processing apparatus according to claim 1, wherein the tallying unit tallies the information relating to the inclination angle of the imaging device obtained by the obtaining unit at a time when one continuous imaging by the imaging device has ended and a predetermined amount of time without subsequent imaging being started has elapsed.

4. The information processing apparatus according to claim 1, wherein the imaging device is included in the information processing apparatus.

5. The information processing apparatus according to claim 1, further comprising a display control unit configured to display a result of the determination by the determination unit on a display unit.

6. The information processing apparatus according to claim 1, wherein the determination unit determines whether the region imaged by the imaging device is a left side or a right side of a chest.

7. The information processing apparatus according to claim 1, wherein the determination unit performs the determination based on the information relating to the inclination angle obtained at a timing an inclination angle of the imaging device satisfies the predetermined angle condition, while the imaging device is touching the subject.

8. The information processing apparatus according to claim 1, wherein the predetermined angle condition is when an inclination angle of the imaging device with respect to one or more predetermined directions in a coordinate system of a predetermined space becomes greater than or equal to a predetermined angle.

9. An information processing method comprising:
obtaining information relating to an inclination angle of an imaging device that is imaging a region of a subject;
performing a determination, based on the information relating to the inclination angle of the imaging device, regarding which region of the subject corresponds to the region imaged by the imaging device, wherein the determination is performed based on the information relating to the inclination angle obtained at a timing when the inclination angle of the imaging device satisfies a predetermined angle condition; and
generating a tally result by tallying information relating to a plurality of inclination angles of the imaging device obtained in the obtaining,
wherein the determination is performed based on the tally result generated in the generating, and
wherein, in the generating, tallied is the information relating to the inclination angle of the imaging device obtained, in the obtaining, at a time when one continuous imaging by the imaging device ends.

10. A non-transitory computer-readable storage medium storing a computer program for causing a computer to execute an information processing method, the method comprising:
obtaining information relating to an inclination angle of an imaging device that is imaging a region of a subject;
performing a determination, based on the information relating to the inclination angle of the imaging device, regarding which region of the subject corresponds to the region imaged by the imaging device, wherein the determination is performed based on the information relating to the inclination angle obtained at a timing when the inclination angle of the imaging device satisfies a predetermined angle condition; and
generating a tally result by tallying information relating to a plurality of inclination angles of the imaging device obtained in the obtaining,
wherein the determination is performed based on the tally result generated in the generating, and
wherein, in the generating, tallied is the information relating to the inclination angle of the imaging device obtained, in the obtaining, at a time when one continuous imaging by the imaging device ends.

11. An information processing apparatus comprising:
a memory storing a program; and
one or more processors that, by executing the program, function as:
   (a) an obtaining unit configured to obtain information relating to an inclination angle of an imaging device that is imaging a region of a subject; and (b) a determination unit configured to perform a determination, based on the information relating to the inclination angle of the imaging device, regarding which region of the subject corresponds to the region imaged by the imaging device, wherein the determination unit performs the determination based on the information relating to the inclination angle obtained at a timing when the inclination angle of the imaging device satisfies a predetermined angle condition, wherein the predetermined angle condition is when the imaging device is stationary for a predetermined amount of time or more at a predetermined angle or more.

12. An information processing apparatus comprising:
a memory storing a program; and
one or more processors that, by executing the program, function as:
   (a) an obtaining unit configured to obtain information relating to an inclination angle of an imaging device that is imaging a region of a subject; and
   (b) a determination unit configured to perform a determination, based on the information relating to the inclination angle of the imaging device, regarding which region of the subject corresponds to the region imaged by the imaging device, wherein the determination unit performs the determination based on the information relating to the inclination angle obtained at a timing when the inclination angle of the imaging device satisfies a predetermined angle condition, wherein the determination unit determines whether the region imaged by the imaging device is a left side or a right side of a chest, in accordance with whether an inclination angle of the imaging device with respect to one or more predetermined directions in a coordinate system of a predetermined space is positive or negative.

13. An information processing apparatus comprising:
a memory storing a program; and
one or more processors that, by executing the program, function as:
   (a) an obtaining unit configured to obtain information relating to an inclination angle of an imaging device that is imaging a region of a subject;
   (b) a determination unit configured to perform a determination, based on the information relating to the inclination angle of the imaging device, regarding which region of the subject corresponds to the region imaged by the imaging device, wherein the determination unit performs the determination based on the information relating to the inclination angle obtained at a timing when the inclination angle of the imaging device satisfies a predetermined angle condition; and
   (c) a tallying unit configured to generate a tally result by tallying information relating to a plurality of inclination angles of the imaging device obtained by the obtaining unit,
wherein the determination unit performs the determination based on the tally result generated by the tallying unit,
wherein the tallying unit generates information indicating a distribution of inclination angles of the imaging device as the tally result, and
wherein the information indicating a distribution of inclination angles of the imaging device comprises at least one of an average value, a median value, and a histogram of the plurality of inclination angles.

* * * * *